United States Patent
Sana et al.

(10) Patent No.: US 11,207,017 B2
(45) Date of Patent: Dec. 28, 2021

(54) SYSTEM AND METHOD FOR NON-INVASIVE EXTRACTION OF FETAL ELECTROCARDIOGRAM SIGNALS

(71) Applicant: King Abdullah University of Science and Technology, Thuwal (SA)

(72) Inventors: Furrukh Sana, Thuwal (SA); Tarig Ballal Khidir Ahmed, Thuwal (SA); Ibrahim Hoteit, Thuwal (SA); Tareq Yousef Al-Naffouri, Thuwal (SA)

(73) Assignee: KING ABDULLAH UNIVERSITY OF SCIENCE AND TECHNOLOGY, Thuwal (SA)

(*) Notice: Subject to any disclaimer, the term of this patent is extended or adjusted under 35 U.S.C. 154(b) by 90 days.

(21) Appl. No.: 16/468,855

(22) PCT Filed: Dec. 12, 2017

(86) PCT No.: PCT/IB2017/057853
§ 371 (c)(1),
(2) Date: Jun. 12, 2019

(87) PCT Pub. No.: WO2018/109669
PCT Pub. Date: Jun. 21, 2018

(65) Prior Publication Data
US 2019/0313929 A1    Oct. 17, 2019

Related U.S. Application Data

(60) Provisional application No. 62/433,504, filed on Dec. 13, 2016.

(51) Int. Cl.
*A61B 5/344*        (2021.01)
*A61B 5/35*         (2021.01)
(Continued)

(52) U.S. Cl.
CPC .............. *A61B 5/344* (2021.01); *A61B 5/327* (2021.01); *A61B 5/35* (2021.01); *A61B 5/02411* (2013.01);
(Continued)

(58) Field of Classification Search
CPC .............. A61B 5/0444; A61B 5/04028; A61B 5/04525; A61B 5/02411; A61B 5/7267;
(Continued)

(56) References Cited

U.S. PATENT DOCUMENTS 5,372,139 A * 12/1994 Holls ................... A61B 5/4362
                                                         600/511
10,987,047 B2 * 4/2021 Principe ................. G16Z 99/00
(Continued)

OTHER PUBLICATIONS

Single channel fetal ECG recovery using sparse redundant representations, Signals, Circuits and Systems, 2011 10th International Symposium on, IEEE, Jun. 30, 2011 (Year: 2011).*
(Continued)

*Primary Examiner* — Christopher A Flory
(74) *Attorney, Agent, or Firm* — Billion & Armitage

(57) ABSTRACT

A method of estimating fetal electrocardiogram (FECG) signals utilizes a plurality of ECG signals measured along the mother's abdomen. The method includes defining an MECG (ECG) dictionary of symbols and projecting the plurality of abdominal ECG signals onto the MECG dictionary to estimate MECG signals within each of the plurality of abdominal ECG signals. The estimated MECG signals are subtracted from the plurality of measured abdominal ECG signals to estimate FECG signals and the plurality of estimated FECG signals are combined to generate a representation of the FECG source signal.

18 Claims, 12 Drawing Sheets

(51) Int. Cl.
　　　A61B 5/327　　　(2021.01)
　　　A61B 5/024　　　(2006.01)
　　　A61B 5/00　　　 (2006.01)
(52) U.S. Cl.
　　　CPC ......... *A61B 5/7267* (2013.01); *A61B 2503/02* (2013.01)
(58) Field of Classification Search
　　　CPC ..... A61B 2503/02; A61B 5/327; A61B 5/344; A61B 5/35
　　　See application file for complete search history.

(56) References Cited

U.S. PATENT DOCUMENTS

| | | | | |
|---|---|---|---|---|
| 2002/0193670 | A1* | 12/2002 | Garfield | A61B 5/4362 600/304 |
| 2004/0243015 | A1* | 12/2004 | Smith | A61B 5/344 600/511 |
| 2005/0267376 | A1* | 12/2005 | Marossero | A61B 5/391 600/511 |
| 2005/0267377 | A1* | 12/2005 | Marossero | A61B 5/344 600/511 |
| 2007/0027396 | A1* | 2/2007 | Assaleh | A61B 5/344 600/511 |
| 2007/0233203 | A1* | 10/2007 | Euliano | A61B 5/4356 607/46 |
| 2008/0146953 | A1* | 6/2008 | Kimura | A61B 5/344 600/511 |
| 2008/0183092 | A1* | 7/2008 | Smith | A61B 5/4362 600/511 |
| 2009/0182242 | A1* | 7/2009 | Moses | A61B 5/02411 600/511 |
| 2009/0192396 | A1* | 7/2009 | Hayes-Gill | A61B 5/02411 600/511 |
| 2009/0259133 | A1* | 10/2009 | Wolfberg | A61B 5/412 600/511 |
| 2009/0299212 | A1* | 12/2009 | Principe | A61B 5/1107 600/547 |
| 2010/0137727 | A1* | 6/2010 | Sameni | A61B 5/7203 600/511 |
| 2010/0185108 | A1* | 7/2010 | Vullings | A61B 5/4362 600/511 |
| 2011/0192398 | A1* | 8/2011 | Euliano | A61B 5/7221 128/203.14 |
| 2012/0016209 | A1* | 1/2012 | Wolfberg | A61B 5/412 600/301 |
| 2012/0083676 | A1* | 4/2012 | Wolfberg | A61B 5/4362 600/301 |
| 2012/0150010 | A1* | 6/2012 | Hayes-Gill | A61B 5/4343 600/382 |
| 2012/0150053 | A1* | 6/2012 | Hayes-Gill | A61B 5/02411 600/511 |
| 2012/0238894 | A1* | 9/2012 | Principe | A61B 5/1107 600/546 |
| 2013/0096394 | A1* | 4/2013 | Gupta | G06K 9/00536 600/301 |
| 2013/0102856 | A1* | 4/2013 | Wolfberg | A61B 5/344 600/301 |
| 2013/0102857 | A1* | 4/2013 | Wolfberg | A61B 5/6823 600/301 |
| 2014/0005988 | A1* | 1/2014 | Brockway | A61B 5/349 703/2 |
| 2014/0136585 | A1* | 5/2014 | Brockway | G06K 9/0051 708/317 |
| 2014/0142894 | A1* | 5/2014 | Chang | G06F 17/18 702/181 |
| 2014/0194758 | A1* | 7/2014 | Korenberg | A61B 5/7203 600/509 |
| 2014/0350421 | A1* | 11/2014 | Sameni | A61B 5/7203 600/511 |
| 2015/0112220 | A1* | 4/2015 | Sana | H04B 1/7163 600/527 |
| 2016/0022164 | A1* | 1/2016 | Brockway | A61B 5/725 600/509 |
| 2016/0198969 | A1* | 7/2016 | Cheng | A61B 5/02411 600/511 |
| 2016/0270670 | A1* | 9/2016 | Oz | A61B 5/7203 |
| 2016/0310062 | A1* | 10/2016 | Larson | A61B 5/4362 |
| 2017/0007142 | A1* | 1/2017 | Oz | A61B 5/7203 |
| 2017/0055866 | A1* | 3/2017 | Vullings | A61B 5/344 |
| 2017/0172426 | A1* | 6/2017 | Oz | A61B 5/7203 |
| 2017/0360377 | A1* | 12/2017 | Rossi | A61B 5/364 |
| 2019/0059767 | A1* | 2/2019 | Oz | A61B 5/344 |
| 2019/0125246 | A1* | 5/2019 | Principe | A61B 5/391 |
| 2020/0022597 | A1* | 1/2020 | Cheng | A61B 5/316 |

OTHER PUBLICATIONS

Notification of Transmittal of the International Search Report and the Written Opinion of the International Searching Authority, or the Declaration for PCT/IB2017/057853 dated Mar. 8, 2018.

Ciocoiu, "Single channel fetal ECG recovery using sparse redundant representations", Signals, Circuits and Systems (ISSCS), 10th International Symposium on, IEEE, Jun. 30, 2011, 1-4.

Da Poian, et al., "Separation and Analysis of Fetal-ECG Signals from Compressed Sensed Abdominal ECG Recordings", IEEE Transaction on Biomedical Engineering, IEEE Service Center, Piscathaway, NJ, USA, vol. 63, No. 6, Jun. 1, 2016, 1269-1279.

Maier, "Fetal QRS detection and RR interval measurement in noninvasively registered abdominal ECGs", Computing in Cardiology 2013, n/a,, Sep. 22, 2013, 165-168.

Addison, "Wavelet Transforms and the ECG: A Review", Physiological Measurement, vol. 26, No. 5, Aug. 8, 2005, pp. R155-R199.

Aharon, et al., "K-SVD: An Algorithm for Designing Overcomplete Dictionaries for Sparse Representation", IEEE Transactions on Signal Processing, vol. 54, No. 11, Nov. 2006, pp. 4311-4322.

Behar, et al., "A Comparison of Single Channel Foetal ECG Extraction Methods", Annals of Biomedical Engineering, vol. 42, 2014, 33 pages.

Camargo-Olivares, et al., "The Maternal Abdominal ECG as Input to MICA in the Fetal ECG Extraction Problem", IEEE Signal Processing Letters, vol. 18, Issue 3, Jan. 10, 2011, pp. 161-164.

Castro, et al., "A Method for Context-Based Adaptive QRS Clustering in Real Time", IEEE Journal of Biomedical and Health Informatics, vol. 19, Issue 5, Oct. 8, 2014, 12 pages.

Escoda, et al., "Ventricular and Atrial Activity Estimation Through Sparse ECG Signal Decompositions", IEEE International Conference on Acoustics Speech and Signal Processing Proceedings, May 14-19, 2006, 7 pages.

Jafari, et al., "Fetal Electrocardiogram Extraction by Sequential Source Separation in the Wavelet Domain", IEEE Transactions on Biomedical Engineering, vol. 52, No. 3, Mar. 2005, pp. 390-400.

Lathauwer, et al., "Fetal Electrocardiogram Extraction by Source Subspace Separation", Proceedings IEEE SP/Athos Workshop on Higher-Order Statistics, Jun. 12-14, 1995, pp. 134-138.

Marzbanrad, et al., "Model-Based Estimation of Aortic and Mitral Valves Opening and Closing Timings in Developing Human Fetuses", IEEE Journal of Biomedical and Health Informatics, vol. 20, Issue 1, Oct. 16, 2014, pp. 240-248.

Masood, et al., "Support Agnostic Bayesian Recovery of Jointly Sparse Signals", 2014 22nd European Signal Processing Conference (EUSIPCO), IEEE, 2014, 5 pages.

Mazomenos, et al., "A Low-Complexity ECG Feature Extraction Algorithm for Mobile Healthcare Applications", IEEE Journal of Biomedical and Health Informatics, vol. 17, No. 2, Mar. 2013, pp. 459-469.

Mcsharry, et al., "A Dynamical Model for Generating Synthetic Electrocardiogram Signals", IEEE Transactions on Biomedical Engineering, vol. 50, No. 3, Mar. 2003, pp. 289-294.

Niknazar, et al., "Fetal ECG Extraction by Extended State Kalman Filtering Based on Single-Channel Recordings", IEEE Transactions on Biomedical Engineering, Institute of Electrical and Electronics Engineers, vol. 60, 2013, 8 pages.

Reisner, et al., "The Physiological Basis of the Electrocardiogram", Biomedical Signal and Image Processing, 2007, pp. 1-25.

(56) References Cited

OTHER PUBLICATIONS

Rooijakkers, et al., "Feasibility Study of a New Method for Low-Complexity Fetal Movement Detection from Abdominal ECG Recordings", IEEE Journal of Biomedical and Health Informatics, vol. 20, Issue 5, Sep. 2016, 8 pages.
Sameni, et al., "What ICA Provides for ECG Processing: Application to Noninvasive Fetal ECG Extraction", IEEE International Symposium on Signal Processing and Information Technology, Sep. 2006, 6 pages.
Sato, et al., "A Novel Extraction Method of Fetal Electrocardiogram from the Composite Abdominal Signal", IEEE Transactions on Biomedical Engineering, vol. 54, Issue 1, Jan. 2007, pp. 49-58.
Shadaydeh, et al., "Extraction of Fetal ECG Using Adaptive Volterra Filters", 16th European Signal Processing Conference (EUSIPCO 2008), Aug. 25-29, 2008, 5 pages.
Vigneron, et al., "Fetal Electrocardiogram Extraction Based on Non-Stationary ICA and Wavelet Denoising", 7th IEEE International Symposium on Signal Processing and its applications, Jul. 2003, 4 pages.
Wenting, et al., "FECG Extraction Based on BSS of Sparse Signal", 2nd International Conference on Bioinformatics and Biomedical Engineering, May 16-18, 2008, pp. 1457-1460.
Wu, et al., "Research of Fetal ECG Extraction Using Wavelet Analysis and Adaptive Filtering", Computers in Biology and Medicine, vol. 43, Oct. 2013, pp. 1622-1627.
Zarzoso, et al., "Noninvasive Fetal Electrocardiogram Extraction: Blind Separation Versus Adaptive Noise Cancellation", IEEE Transactions on Biomedical Engineering, vol. 48, No. 1, Jan. 2001, pp. 12-18.
Zhang, et al., "Compressed Sensing for Energy-Efficient Wireless Telemonitoring of Noninvasive Fetal ECG via Block Sparse Bayesian Learning", IEEE Transactions on Biomedical Engineering, vol. 60, No. 2, 2013, pp. 300-309.

\* cited by examiner

SYSTEM AND METHOD FOR NON-INVASIVE EXTRACTION OF FETAL ELECTROCARDIOGRAM SIGNALS

TECHNICAL FIELD

This invention relates generally to patient monitoring, and in particular to monitoring fetal electrocardiogram (ECG) signal.

BACKGROUND

Monitoring of electrocardiogram signals is utilized in a variety of applications for assessing the health of patients. Throughout the pregnancy, the ECG of the mother may be monitored to assess the health of the mother. However, there is generally no mechanism for monitoring the ECG of the fetus (referred to herein as the FECG). During labor, the ECG of the fetus may be monitored via invasive methods, such as coupling an electrode onto the scalp of the fetus to allow monitoring. However, it would be beneficial to develop a system and method of non-invasively monitoring the FECG signal throughout the pregnancy as well as during labor.

DETAILED DESCRIPTION

This disclosure describes a system and method of extracting the FECG signal from abdominal ECG recordings of the mother by exploiting the support similarities between ECG recordings represented in the sparse domain. In one embodiment, this disclosure utilizes a multiple measurement vector (MMV) approach to estimate the component of the mother's ECG signal (MECG) measured by ECG sensors (in one embodiment, by ECG sensors adhered to the mother's abdomen). Having estimated the MECG component present in the monitored ECG signal, the MECG component can be subtracted to isolate the fetal ECG component (FECG). In embodiments in which a plurality of sensors are utilized and an FECG signal is extracted with respect to each ECG sensor, the plurality of extracted FECG components may be combined by once again utilizing the support similarities between the signals.

Figure 1:
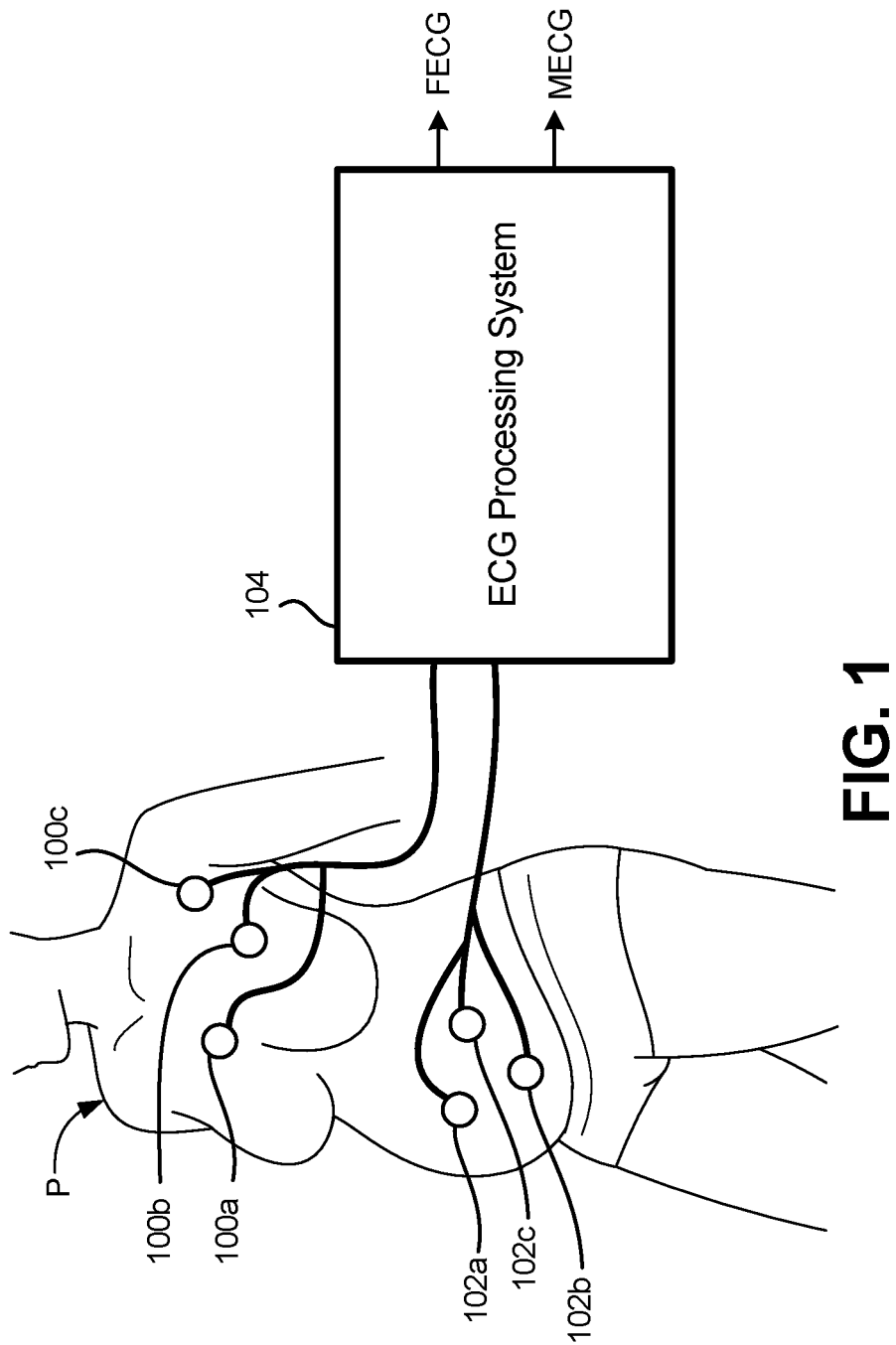
FIG. 1 is a diagram illustrating placement of a first plurality of electrodes at a first location of the patient and a second plurality of electrodes at a second location of the patient according to an embodiment of the present invention.

FIG. 1 is a diagram illustrating placement of first plurality of electrodes and second plurality of electrodes onto a pregnant patient according to an embodiment of the present invention. In the embodiment shown FIG. 1, patient P is outfitted with first plurality of electrodes 100a, 100b and 100c, and second plurality of electrodes 102a, 102b, and 102c. In the embodiment illustrated herein, first plurality of electrodes 100a, 100b, and 100c are adhered to the chest of patient P, while second plurality of electrodes 102a, 102b are adhered to the abdomen of patient P. While the embodiment shown in FIG. 1 utilizes a three electrodes at each location (e.g., chest and abdomen), in other embodiments a different plurality of electrodes may be utilized at each location. In addition, while the term "electrode" is utilized with respect to FIG. 1, in other embodiments the electrodes may be referred to as ECG monitoring devices. In addition, while in the embodiments shown in FIG. 1 the electrodes or ECG monitoring devices are adhered to the skin of the patient P, in other embodiments the electrodes may be located subcutaneously. In other embodiments, the plurality of electrodes may be embedded in fabric/clothing to enable a wearable embodiment.

MOM With respect to the first plurality of electrodes 100a, 100b, 100c (referred to herein as "chest electrodes" due to their location in this embodiment), chest ECG signals are monitored. Likewise, with respect to the second plurality of electrodes 102a, 102b, and 102c (referred to herein as "abdominal electrodes"), abdominal ECG signals are monitored. In other embodiments, the first and second plurality of electrodes may be placed at different locations on patient P. However, a benefit of locating the first plurality of electrodes 100a, 100b, and 100c on the chest of patient P is that the monitored chest ECG signals are representative of the MECG signal. The abdominal ECG signals—due to the proximity to the fetus—will contain components of both the MECG and FECG signal. Monitored ECG signals are provided to ECG processing system 104 for processing, which includes extraction of FECG signal associated with the fetus. Processing may also include extraction of the MECG signal.

As discussed in more detail below, ECG processing system 104 may include a combination of hardware and software for processing the received ECG signals. Hardware may include analog circuitry, digital circuitry and/or microprocessors capable of executing software (e.g., CPU, GPU, etc.). In general, ECG processing system 104 utilizes the chest ECG signals to learn a dictionary of symbols utilized to represent the MECG signal in the sparse domain. Having learned the suitable dictionary of symbols, the abdominal ECG signals can be projected onto the dictionary to obtain a sparse representation of the MECG component of the monitored abdominal ECG signals. Subsequently, a sparse signal estimation framework (e.g., multiple measurement vector (MMV) framework) utilizes common support (i.e., similarities) between the MECG components of the monitored abdominal ECG signals in order to estimate and reconstruct the time domain representation of the MECG component present in each of the abdominal ECG signals. Subsequently, the MECG component can be subtracted or removed from the abdominal signal, leaving the FECG component of each monitored abdominal ECG signal. The FECG signals extracted from each monitored abdominal ECG signal can be further processed using a sparse signal estimation framework and the same joint support characteristics that exist between the plurality of estimated FECG signals to infer a single, and more accurate estimate of the FECG signal. This may include operations to combine the FECG component estimated with respect to each monitored abdominal ECG signal. The signal processing utilized is discussed in more detail with respect to FIGS. 3-5, below.

Figure 2:
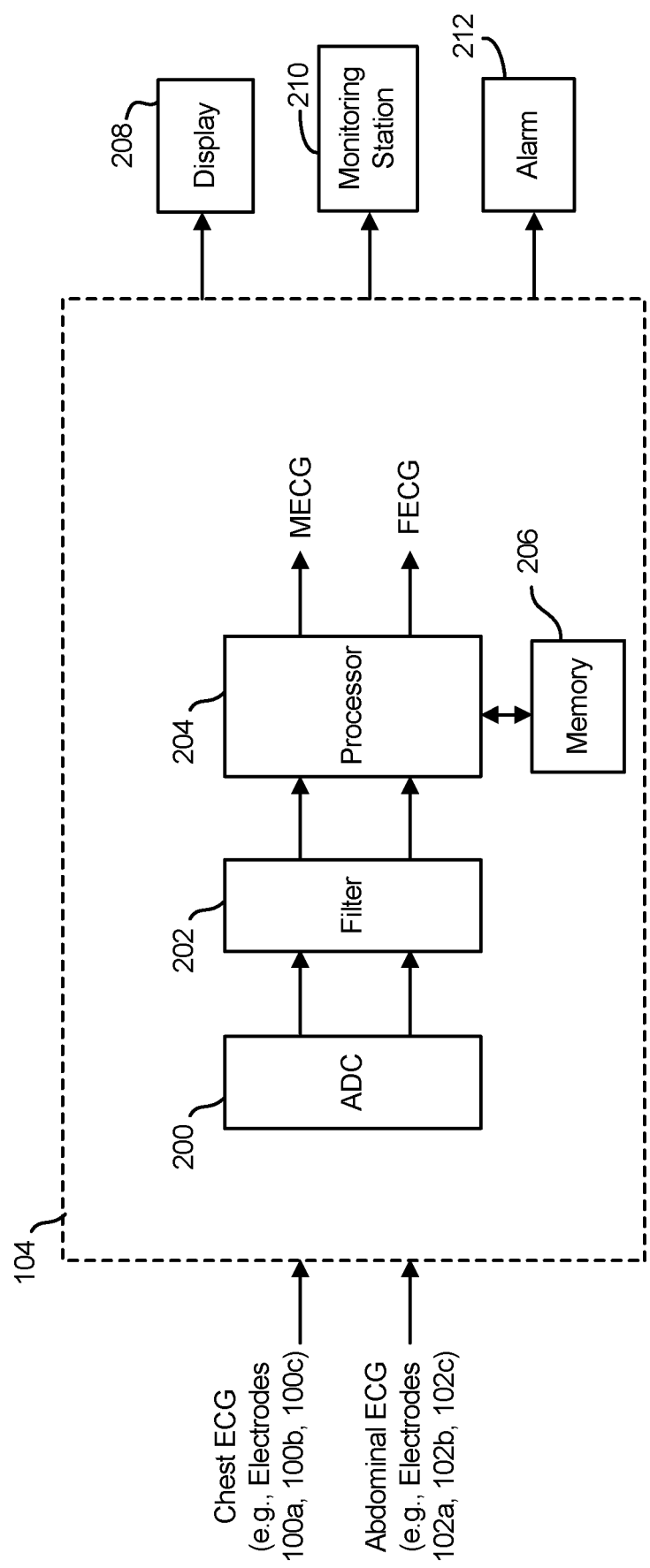
FIG. 2 is a block diagram of a processing system utilized to monitor first and second electrocardiogram signals and extract the fetal ECG (FECG) from the monitored first and second electrocardiogram signals according to an embodiment of the present invention.

FIG. 2 is a block diagram of a processing system utilized to monitor first and second electrocardiogram signals and extract the fetal ECG (FECG) from the monitored first and second electrocardiogram signals according to an embodiment of the present invention. In the embodiment shown in FIG. 2, ECG processing system 104 includes analog-to-digital converter (ADC) 200, filter 202, processor 204, and computer-readable memory 206.

In the embodiment shown in FIG. 2, chest ECG signals and abdominal ECG signals are received by ECG processing system 104, although as discussed above in other embodiments, additional ECG signals may be received and ECG signals need not necessarily be located on the patient's chest and abdomen. In the embodiment shown in FIG. 2, the chest ECG signals are measured by electrodes 100a, 100b, and 100c. Because the ECG signal is monitored at the patient's chest, the predominant factor in the monitored chest ECG is the cardiac activity of patient P (i.e., the MECG signal). The abdominal ECG signals are monitored by electrodes 102a, 102b, and 102c. Due to the location of electrodes 102a, 102b, and 102c, the abdominal ECG signals contain elements of both the MECG and FECG signals.

Figure 3:
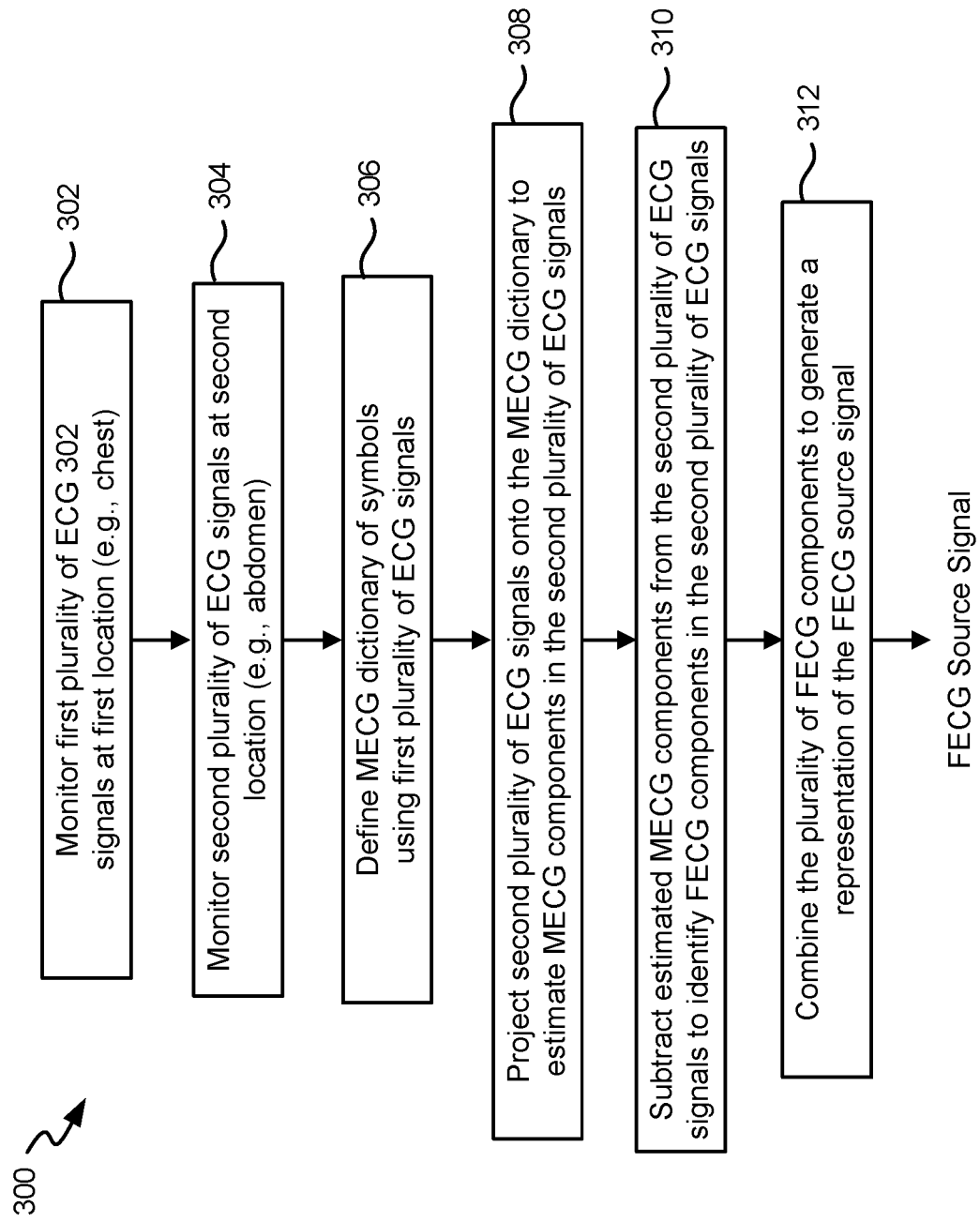
FIG. 3 is a flowchart illustrating processing of the monitored first and second electrocardiogram signals to extract the FECG signal according to an embodiment of the present invention.
Figure 4:
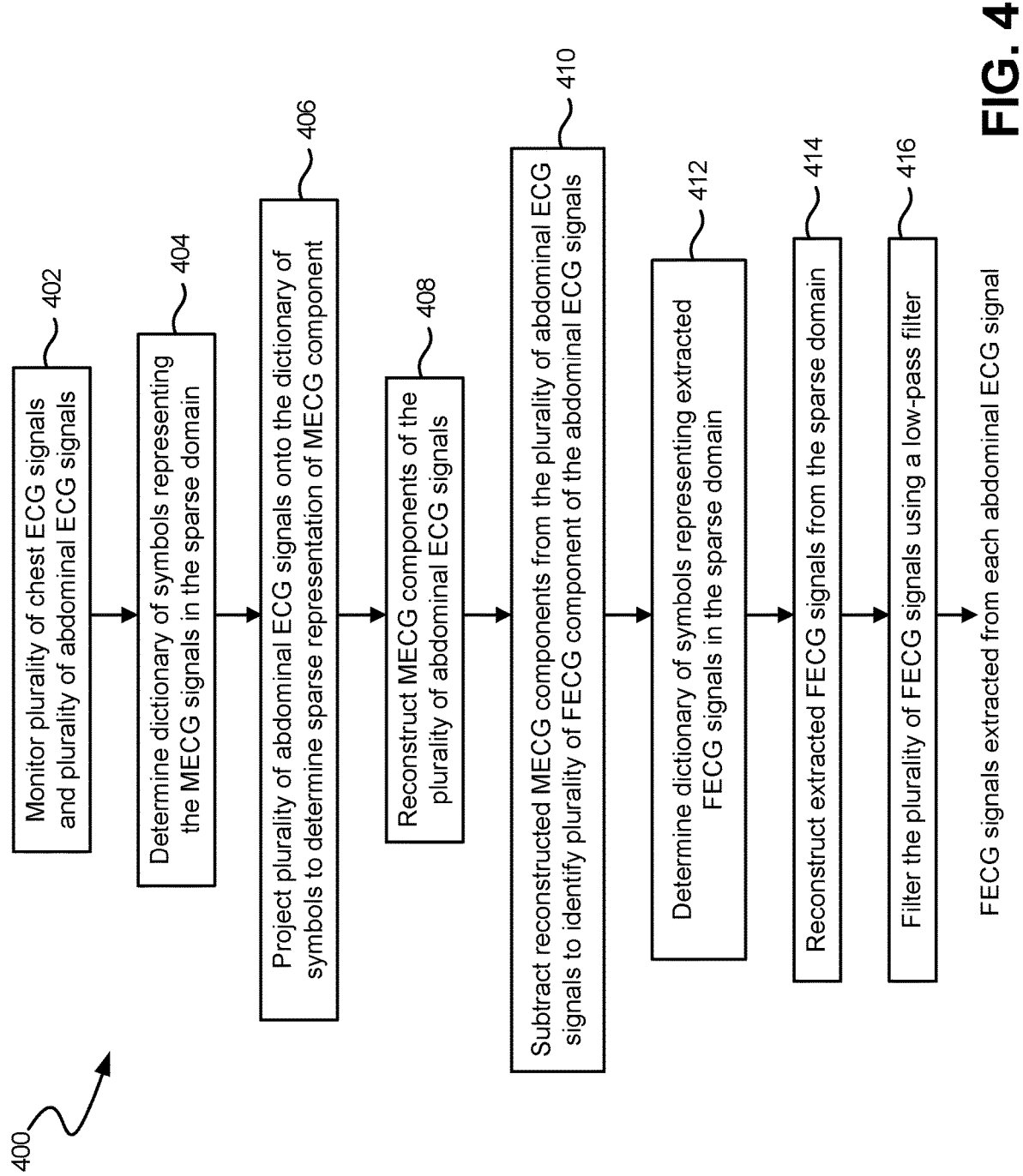
FIG. 4 is a flowchart illustrating processing of the monitored first and second electrocardiogram signals to extract the FECG signal according to another embodiment of the present invention.
Figure 5:
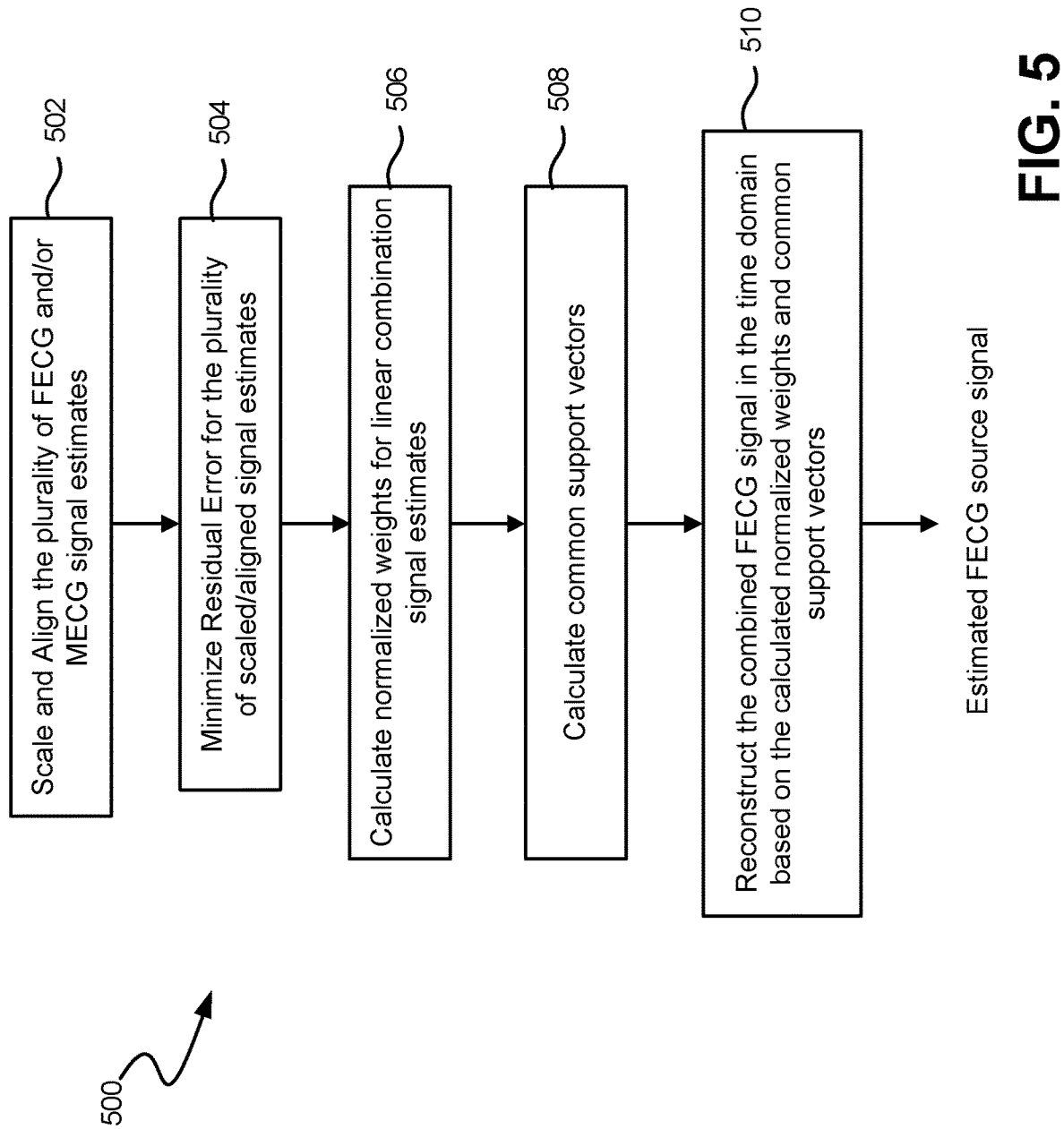
FIG. 5 is a flowchart illustrating the combination of a plurality of recovered FECG signals according to an embodiment of the present invention.

In the embodiment shown in FIG. 2, ADC 200 converts the analog ECG signals to a digital representation. Filter 202 filters the signals and provides the filtered signals to processor 204 (e.g., CPU, GPU, etc.). In one embodiment, processor 204 receives the plurality of chest and abdominal ECG signals and executes instructions stored on non-transitory computer readable memory 204 to implement steps for extracting the FECG signal from the received plurality of ECG signals. Extraction of the FECG signal may also include extraction of the MECG signal. FIGS. 3-5 provide additional details regarding steps and functions implemented by processor 204 to extract the FECG signal from the first and second received ECG signals.

Having extracted the FECG and/or MECG signals, ECG processing system 104 provides them as an output to display 208, monitoring station 210, and/or alarm 212. In one embodiment, display 208 is a digital display or screen that provides a visual representation of the FECG and/or MECG signal. This may include the representation of each beat as well as various values/parameters such as heart rate extracted from the FECG and/or MECG signals.

Monitoring station 210 may include a local monitoring station such as a nurse's station, or a remote monitoring station. Alarm 212 may be a visual or auditory alarm, and be located locally or remotely. For example, in one embodiment, alarm 212 may be located at monitoring station 210 to alert health care providers (e.g., doctor, nurse) that a FECG indicates a heart rate below or above a desired threshold. In one embodiment, one or more of display 208, monitoring station 210 or alarm 212 may be implemented via a smartphone or similar handheld device wireless coupled to ECG processing system 104. In one embodiment, the smartphone or similar device may be utilized to record monitored ECG and FECG signals over a period of time, and may also communicated monitored ECG and/or FECG signals, or data collected via processing of these signals, to a physician as necessary. Communication between ECG processing system 104 and the smartphone or handheld device may be via wireless means (e.g., WiFi, Bluetooth, etc.).

FIG. 3 is a flowchart illustrating processing of the plurality of chest and abdominal ECG signals to extract the FECG signal according to an embodiment of the present invention. At step 302, one or more chest ECG signals are monitored. As discussed above, in this embodiment the ECG signal is monitored at the patient's chest, but in other embodiments may be monitored at other satisfactory locations.

At step 304, a plurality of abdominal ECG signals are monitored. As discussed above, in this embodiment ECG monitoring is provided on the patient's abdomen due to the proximity to the fetus, but in other embodiments the ECG sensors may be located at another location on the patient that results in the monitored ECG signal including the FECG component. In one embodiment, the plurality of chest ECG signals are monitored contemporaneously with the plurality of abdominal ECG signals. In other embodiments, the plurality of chest ECG signals may be monitored independent of the plurality of abdominal ECG signals as discussed below.

At step 306, an MECG dictionary of symbols $\Psi_M$ are defined based on the chest ECG signals. Although in this embodiment ECG signals are monitored at the patient's chest, any location in which an accurate representation of the mother's ECG signal can be obtained would be desirable. In particular, by monitoring at the patient's chest, the proximity of the sensors to the mother's heart results in the monitored ECG signals providing a good representation of the MECG signals. In addition, because the sensors are not located very close to the fetus, the FECG component of the monitored ECG signals is insignificant and may be modeled as noise. In this way, the MECG dictionary is defined and can be utilized in subsequent steps to efficiently and accurately represent the MECG signal in a sparse domain.

At step 308, the second plurality of ECG signals are projected onto the MECG dictionary defined at step 306 to estimate MECG components in the second plurality of ECG signals. In one embodiment, the projection utilizes a sparse signal estimation framework such as a multiple measurement vector (MMV) framework to obtain a sparse representation of the MECG component associated with each of the second plurality of ECG signals. The MMV framework is also utilized to reconstruct the sparse representation of the MECG components into time domain representations of the MECG component included in the second plurality of ECG signals.

At step 310, having estimated the MECG component included in each of the plurality of abdominal ECG signals, the estimated MECG components are subtracted from the plurality of abdominal ECG signals to isolate the FECG components associated with each abdominal ECG signal. As discussed in more detail with respect to FIG. 4, this may include providing further filtering of the plurality of FECG components. For example, in one embodiment, the plurality of FECG components and shared support between the plurality of FECG components are utilized in a multiple measurement vector (MMV) framework utilizing a second dictionary of symbols in order to minimize the effects of distortion.

At step 312, the plurality of FECG components are combined to generate a representation of the FECG source signal. As discussed in more detail with respect to FIG. 5, in one embodiment this includes scaling and aligning of the plurality of FECG signals, and calculating a residual error that quantifies the quality of the signals estimated from each signal. Once again, common support between the plurality of measured FECG signals can be determined and utilized to combine the plurality of FECG signals into a signal representation of the FECG source signal.

FIG. 4 describes in more detail the steps utilized to extract the FECG signal from the plurality of abdominal ECG signals. FIG. 5 describes in more detail the steps utilized to combine the plurality of individual FECG estimates into an estimate of the FECG source signal.

FIG. 4 is a flowchart illustrating processing of the monitored first and second electrocardiogram signals to extract the FECG signal according to another embodiment of the present invention. In particular, FIG. 4 illustrates additional details regarding steps utilized to extract the FECG signal according to an embodiment of the present invention.

The embodiment described with respect to FIG. 4 formulates the problem as a joint estimation of the fetal ECG signal. To this end, the MECG signal 'm' is a sparse domain using an over-complete dictionary $\Psi_M$, which can be expressed as follows:

$$m = \Psi_M d_M \quad (1)$$

where $d_M$ is a sparse vector of coefficients used for representing the MECG signal in ale sparse domain given by the basis elements for the matrix $\Psi_M$. The MECG signal m is measured directly using electrodes placed on the chest of the patient, and can be expressed as follows:

$$y_M^j = m + w^j \quad (2)$$

wherein $y_M^j$ is the ECG recording monitored at the $j^{th}$ sensor, $w^j$ is the additive white Gaussian noise in the measurement recorded from the $j^{th}$ chest sensor.

Combing equations (1) and (2) provides the following:

$$y_M^j = \Psi_M d_M + w^j \quad (3)$$

In contrast, the ECG signals recorded on the patient's abdomen represent a combination of the MECG signal m superimposed with the fetal ECG signal f and noise $n^i$. Mathematically, this is expressed as follows:

$$y_A^j = m + f + n^i \quad (4)$$

wherein $y_A^j$ is the ECG signal monitored at the $i^{th}$ abdominal sensor for I=1, 2, . . . , N and wherein $n^i$ is additive white Gaussian noise in the measurement from the corresponding sensor. The attenuation of the MECG signal as it travels from the chest of the patient towards the abdomen is assumed negligible and is therefore ignored in the above formulation. As a result, the problem of extracting the FECG signal from the abdominal recordings is converted to estimating the MECG signal component and eliminating it, along with the noise and distortions to recover the FECG component.

At step 402, ECG signals are monitored at two or more locations, including at least a first ECG signal and a second ECG signal. In one embodiment, the first ECG signal is monitored at the patient's chest (as discussed above, and labeled $y_M$) and the second ECG signal is monitored at the patient's abdomen (labeled $y_A$). As discussed above, in some embodiments a first plurality of ECG signals may be monitored at the patient's chest and a second plurality of ECG signals may be monitored at the patient's abdomen.

At step 404, a dictionary of symbols $\Psi_M$ representing the MECG signal in the sparse domain are determined based on the ECG signals $y_M$ monitored at the patient's chest. In one embodiment, a k-means clustering (K-SVD) dictionary learning algorithm is utilized with the ECG signals $y_M$ serving as the training set to define the MECG dictionary $\Psi_M$.

At step 406, having defined the dictionary of symbols $\Psi_M$, the abdominal ECG signal $y_A$ is projected onto the MECG dictionary $\Psi_M$, expressed as:

$$\hat{D}_M = MMV(Y_A, \Psi_M) \quad (5)$$

The projection of the abdominal ECG signal onto the MECG dictionary provides a sparse representation of the MECG component. The estimation problem in the sparse domain is defined as estimating the set of vectors $\hat{D}_M = [\hat{d}_M^1, \hat{d}_M^2, \ldots, \hat{d}_M^N]$ that correspond to the set of abdominal measurements $Y_A$. The FECG signal is consider as noise for the purpose of this step and can be modeled as such.

At step 408, once the set of coefficient vectors $\hat{D}_M$ are estimated, then the MECG signal can be reconstructed as present at the patient's abdomen based on the dictionary of symbols $\Psi_M$ and coefficient vectors $\hat{D}_M$. Mathematically this is represented as follows:

$$\hat{M} = \Psi_M \hat{D}_M \quad (6)$$

At step 410, having reconstructed the MECG component present at the patient's abdomen, the reconstructed MECG signal $\hat{M}$ is subtracted from the abdominal ECG signal $Y_A$ as provided below.

$$\tilde{F} = Y_A - \hat{M} \quad (7)$$

wherein $\tilde{M} = [\tilde{m}^1, \tilde{m}^2, \ldots, \tilde{m}^N]$ and $\tilde{F} = [\tilde{f}^1, \tilde{f}^2, \ldots, \tilde{f}^N]$ represent the mother and fetal ECG signal estimates received from each of the N abdominal sensors, respectively.

While the signal $\tilde{F}$ represents the fetal ECG signal estimate, this estimate will typically contain high levels of noise and distortion. At steps 412 and 414, noise and distortion in the signal is minimized by applying a second dictionary framework. In the embodiment shown in FIG. 4, at step 412 a dictionary of wavelet basis elements $\Psi_{wavelet}$ is selected to ensure that only the signal values representing the fetal ECG signals are preserved in the sparse domain while the effects of distortion are minimized. At step 414, the coefficients $\hat{D}_F$ selected for sparse representation in the wavelet domain are used to generate a distortion free version of the fetal ECG signal, represented as:

$$\hat{F}_{noisy} = \Psi_{wavelet} \hat{D}_F \quad (8)$$

At step 416, the estimated fetal ECG signal $F_{noisy}$ is passed through a low-pass filter $$\hat{F} = LPF(\hat{F}_{noisy}) \quad (9)$$

wherein $\hat{F} = [\hat{f}^1, \hat{f}^2, \ldots, \hat{f}^N]$ represent the final FECG signal estimates from the individual abdominal sensors. In this way, FECG signal estimates are generated based on a plurality of ECG signal monitored on the patient's chest and abdomen.

FIG. 5 is a flowchart that illustrates the combining of fetal ECG signal estimates according to an embodiment of the present invention. In general, the combination of fetal ECG signal estimates includes making a determination of the quality of each of the plurality of estimates, and using those quality determinations to weight each of the plurality of FECG signals. The assigned weights are utilized in the linear combination of the plurality of FECG signals. In addition, the combination of individual sensors relies on the support for each of the individual sensor estimates to be common.

In one embodiment, at step 502, FECG and MECG signal estimates are scaled and aligned such that their combinations regenerates close replicas of the observed abdominal ECG (AECG) signal. In one embodiment, scaling and alignment relies on defining a residual error for each $i^{th}$ abdominal sensor, which is defined as:

$$R^i = \|\hat{y}_A^i - y_A^i\|_2^2 \qquad (10)$$

where, $$\hat{y}_A^i = \alpha \cdot \text{Shift}(\hat{m}^i, \tau_1) + \beta \cdot \text{Shift}(\hat{f}, \tau_2)$$

where $\alpha$ and $\beta$ are the scaling coefficients and $\tau_1$ and $\tau_2$ specify the amount by which the estimated MECG signal $\hat{m}^i$ and FECG signal $\hat{f}^i$ are shifted using the operator Shift(•), respectively. In this way, $\hat{y}_A^i$ represents the combination of the estimated FECG signal and estimated MECG signal at each abdominal sensor (i.e., the estimated abdominal signal), wherein the residual error $R^i$ quantifies the error between the estimated abdominal signal and the measured abdominal signal.

At step 504, the residual error is minimized for each individual sensor estimate. For example, in one embodiment the problem can be formulized as follows:

$$\min_{\alpha, \beta, \tau_1, \tau_2} \|R^i\|_2^2 \qquad (10)$$

for each $i^{th}$ sensor. This equation is solved by constructing a search space over a limited range of values for each of the variables $\alpha$, $\beta$, $\tau_1$, and $\tau_2$ to find the combination yielding the least residual error. In this embodiment, the residual error helps determine the quality of the signals estimated from each sensor collecting ECG data, which as described below is utilized to determine the weights to be assigned to each estimated FECG signal. The residual error is inversely related to the reconstruction quality and hence can be used to determine the weights for the linear combination as $$W^i = \frac{1}{R^i}$$

However, for the sum of weights to equal unity (i.e., one), each weight is normalized as $$W^i = \frac{1/R^i}{1/R^1 + 1/R^2 + \dots 1/R^N}$$

In this way, at step 506 the normalized weights for linear combinations are calculated.

Figure 6:
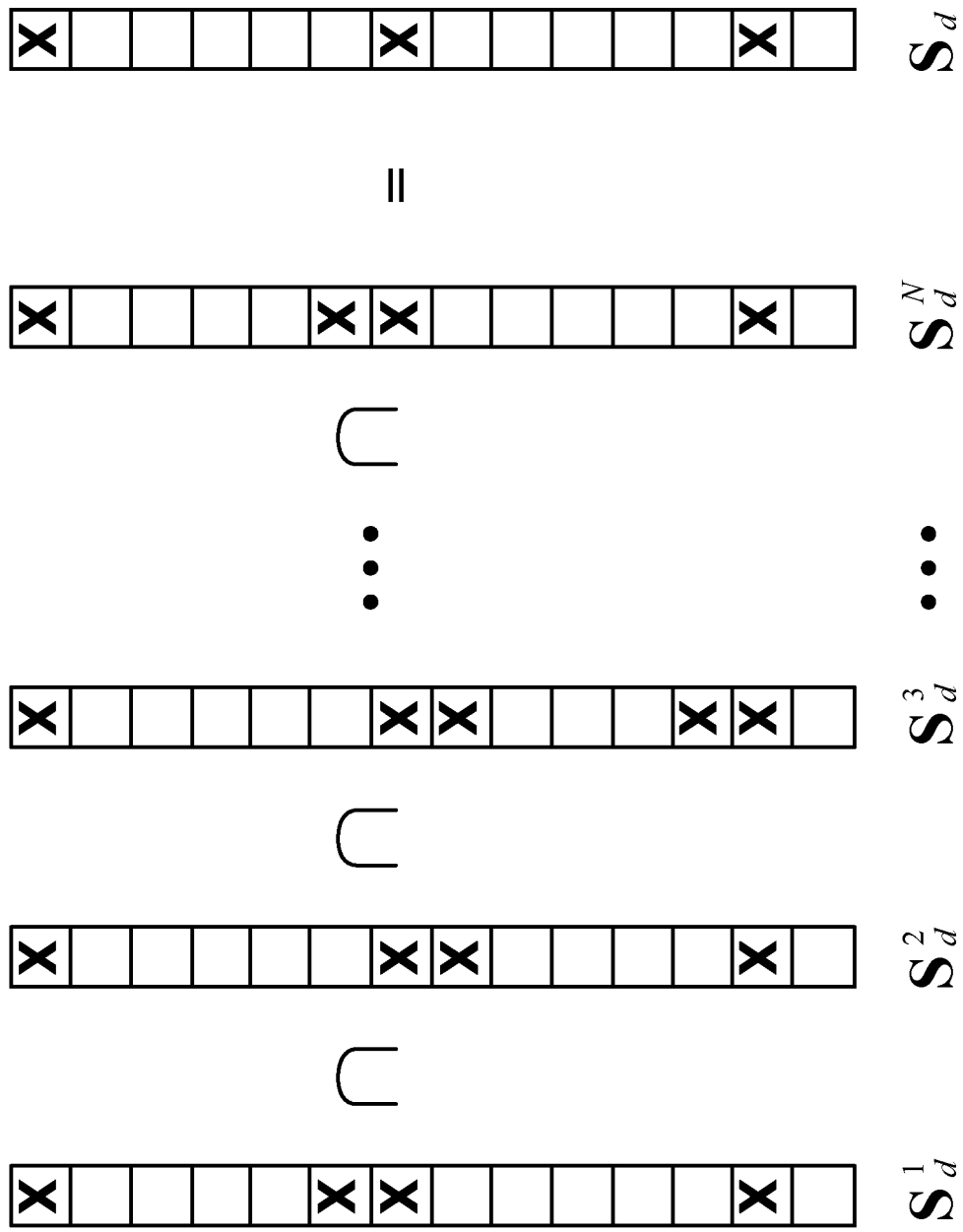
FIG. 6 is a visual representation of determining the common support from the identified support in each of the plurality of estimated FECG signals according to an embodiment of the present invention.

At step 508, common support vectors $S_d$ are calculated. In one embodiment, the determination of the common support may be made using the MMV method. However, in some embodiments the MMV method may provide imperfect common due to small non-zero values at different locations of the estimated vector. In some embodiments, due to the imperfect common support provided, the sensor estimates may be projected onto a domain represented by a simple identify matrix $\Psi_I$ and only those values corresponding to the support locations that are common to all vector of coefficients $d^1, d^2, \dots, d^N$ are retained, while setting the rest to zero. A visual representation of this process is illustrated in FIG. 6, in which the intersection of a plurality of support vectors $S_d^1, S_d^2, S_d^3, \dots, S_d^N$ are shown to obtain $S_d$, which can be expressed mathematically as $$S_d = S_d^1 \cap S_d^2 \dots \cap S_d^N$$

Figure 7:
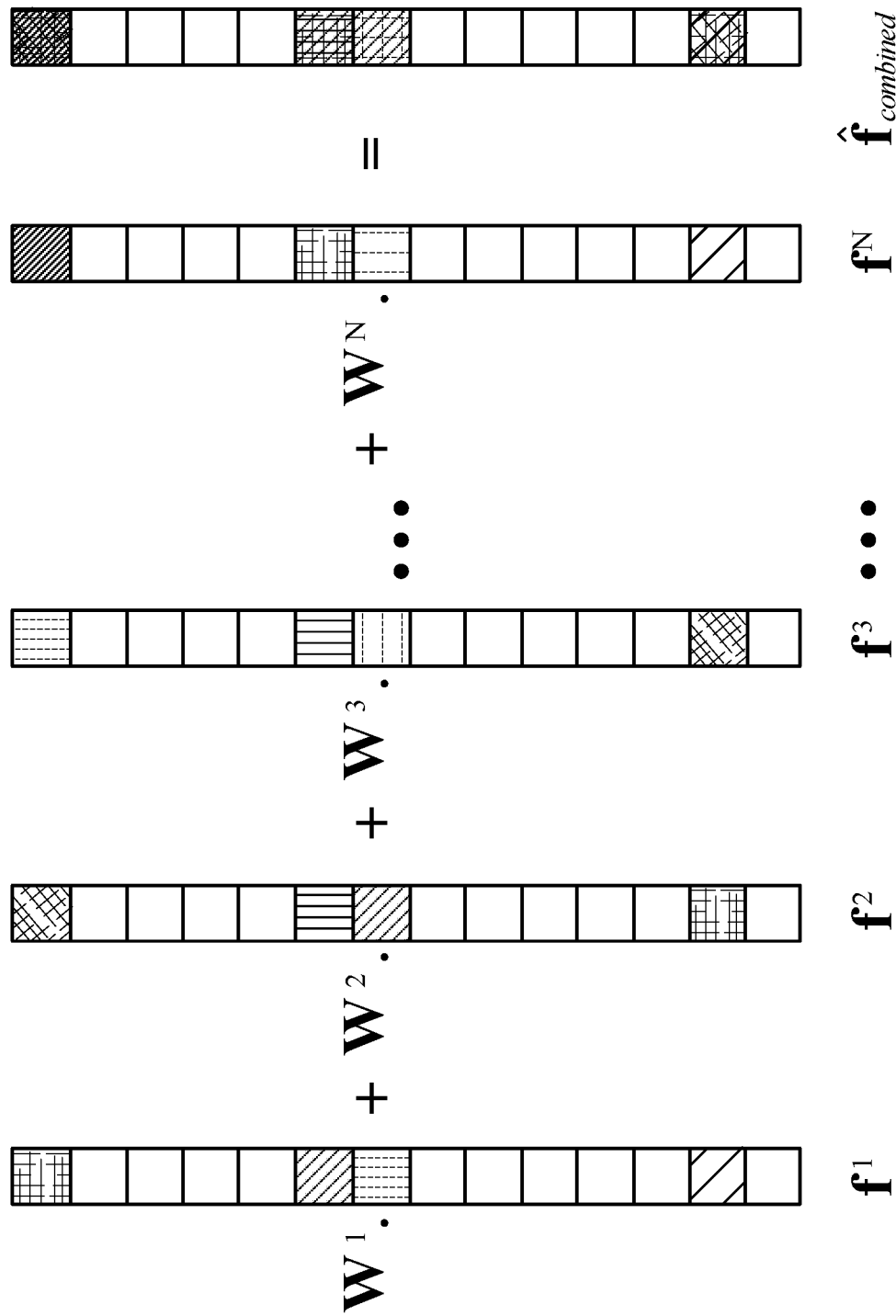
FIG. 7 is a visual representation of the weighted linear combination of the plurality of estimated FECG signals according to an embodiment of the present invention.

At step 510, the combined FECG signal is reconstructed in the time domain. In one embodiment, the reconstructed signal is a function of the common support $S_d$ calculated at step 506 and the normalized weights $W^i$, which is expressed mathematically as $$\hat{f}_{combined} = \Psi_I * (W^1 d_{S_d}^1 + W^2 d_{S_d}^2 + \dots + W^N d_{S_d}^N)$$

wherein the coefficients $d_{S_d}^i$ for the $i^{th}$ signal have non-zero values only at the support locations given by $S_d$. A visual representation of this step is illustrated in FIG. 7, which illustrates the weighted linear combination of the individual FECG signal estimates.

FIGS. 8-17 illustrate experimental results associated with methods of the present invention. Results are based on an embodiment, in which the recorded ECG dataset is comprised of 5 seconds of ECG recordings sampled at a rate of 500 Hz. Furthermore, the experiment relies on three ECG sensors located on the patient's chest to record ECG signals (i.e., three chest ECG signals), and three ECG sensors located on the patient's abdomen to record ECG signals (i.e., three abdominal ECG signals).

Figure 8:
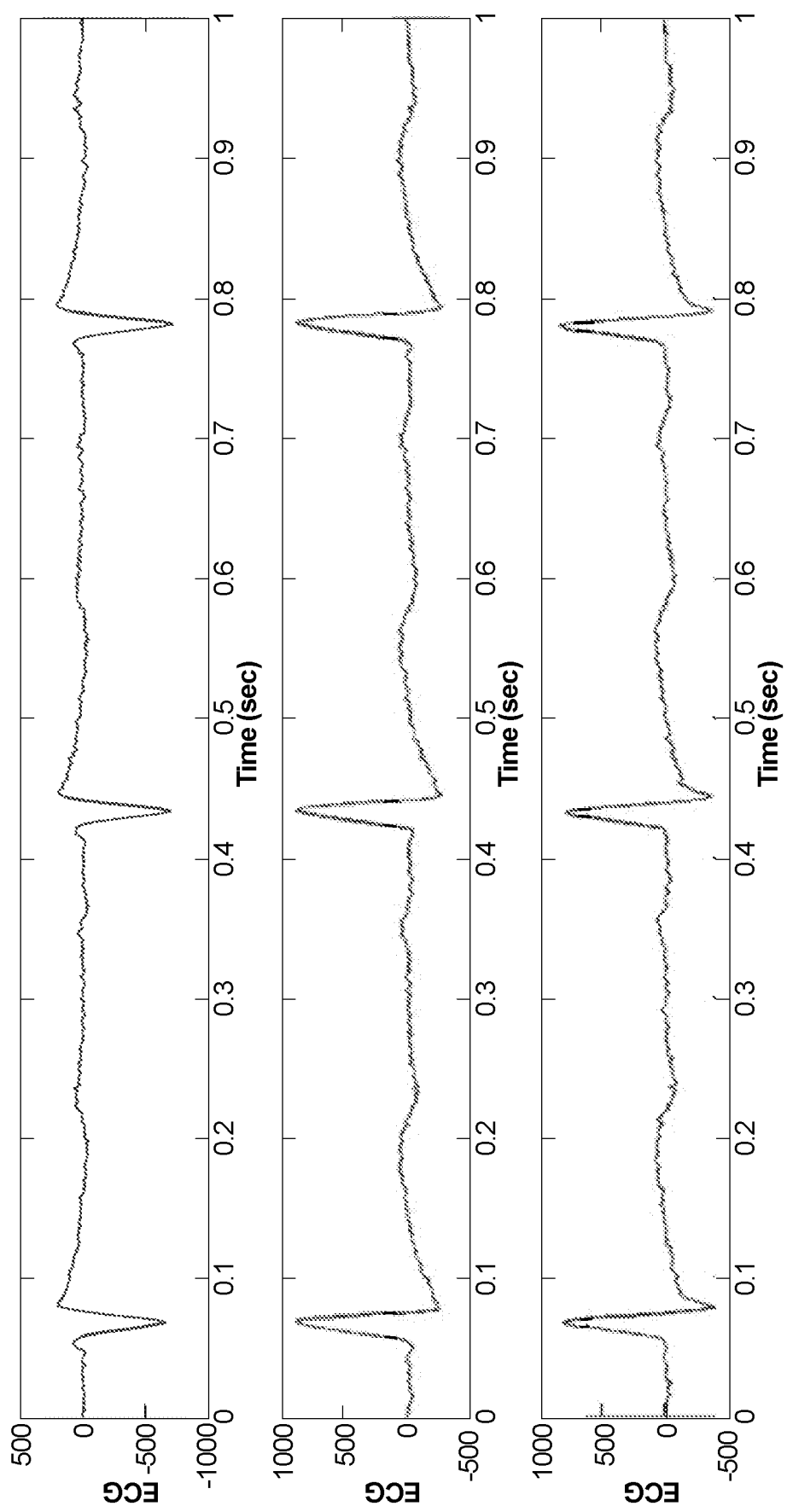
FIG. 8 illustrates ECG signals measured with electrodes located on a patient's chest according to an embodiment of the present invention.

FIG. 8 illustrates the ECG signals recorded with respect to the patient's chest. Due to the proximity of the sensors to the patient's heart, the chest ECG signals are representative of the mother's ECG signal (i.e., MECG). In this embodiment, the MECG dataset is divided into smaller signals using windows of 0.25 second durations that are used as the training set to generate the MECG dictionary of symbols $\Psi_M$ for representing the mother's ECG signal in the sparse domain. In this embodiment, the total number of training signals from the three electrodes is sixty (60), which are then used to generate the dictionary of thirty (30) linearly independent basis elements using the K-SVD algorithm.

Figure 9:
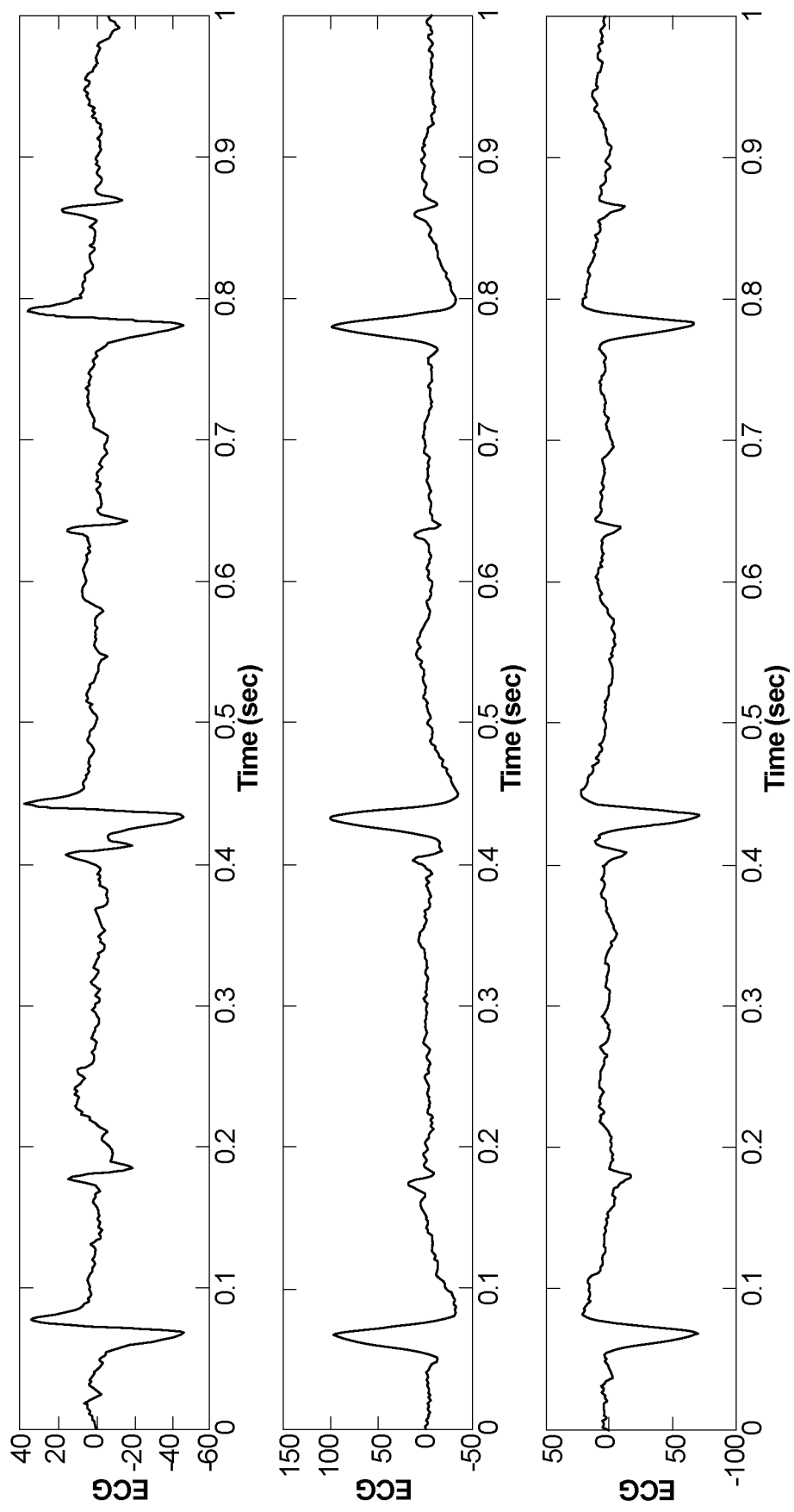
FIG. 9 illustrates the ECG signals measured with electrodes located on a patient's abdomen according to an embodiment of the present invention.

FIG. 9 illustrates the ECG signals recorded with respect to the patient's abdomen. Due to the proximity of the sensors to the fetus, the abdominal ECG signals include a components representative of both the mother's ECG signal (MECG) and the fetal ECG signal (FECG), along with noise and other interference sources.

Figure 10:
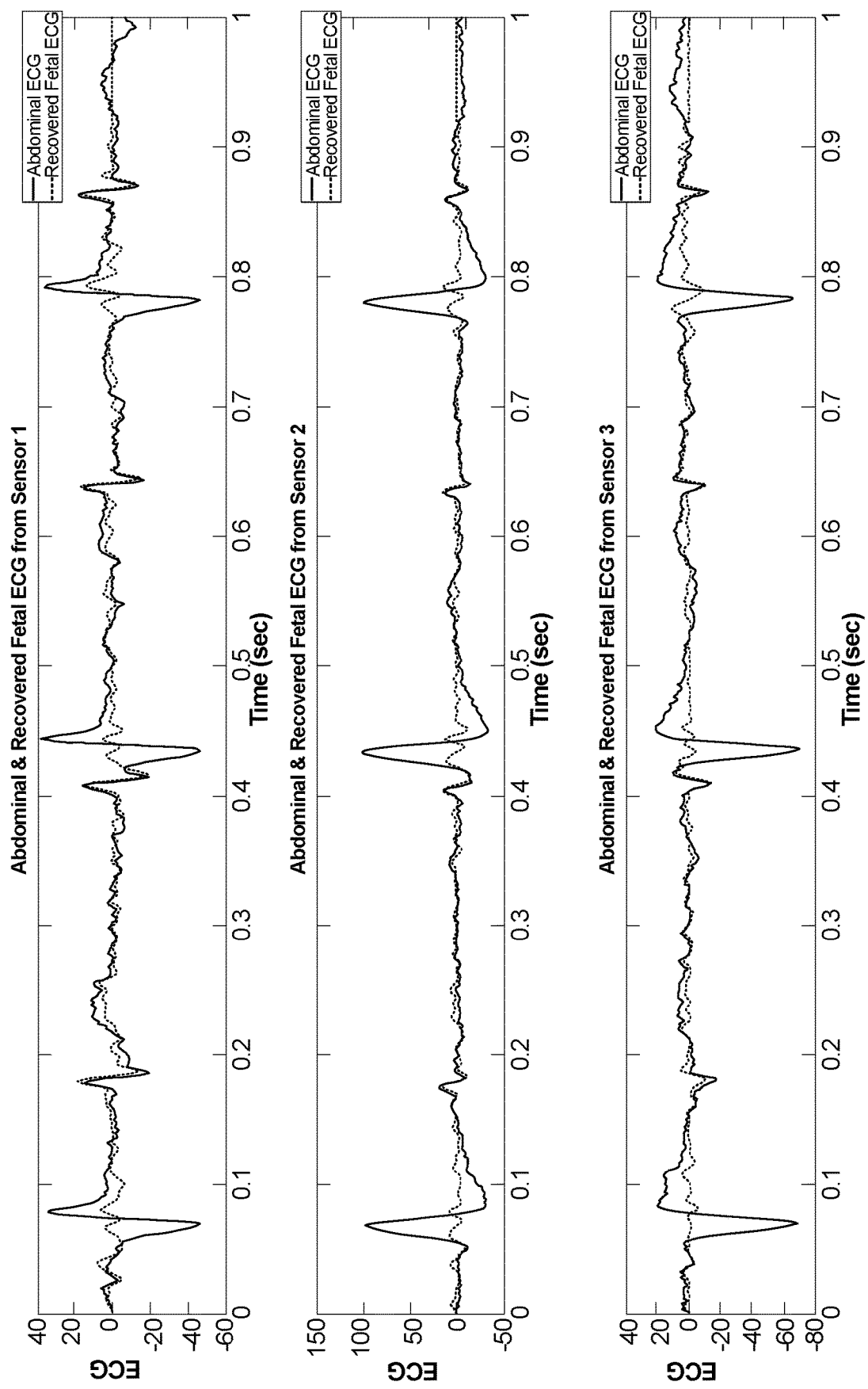
FIG. 10 illustrates the plurality of measured abdominal ECG signals and plurality of estimated fetal ECG signals for each of the plurality of abdominal ECG sensors.

FIG. 10 illustrates the abdominal ECG recorded and recovered fetal ECG for each of the plurality of abdominal ECG sensors. The abdominal ECG signal monitored by each sensor is represented by the blue line and the recovered fetal ECG signal is illustrated by the red line. The recovered fetal ECG signal is generated via application of using the first of the dictionary frameworks to eliminate the MECG signals through sparse domain representation (see, for example, steps 402-410 in FIG. 4). In this particular embodiment, the method includes projecting the abdominal ECG recordings onto the dictionary $\Psi_M$ using a M-SABMP algorithm and subtracting the reconstructed MECG signals from the original abdominal ECG signals. In the example illustrated, a sparsity rate of 25% is used with the M-SABMP algorithm for this step. However, as discussed previously, the individually extracted and reconstructed FECG signals suffer from noise and distortion issues.

To reduce the noise and distortion issues, a second dictionary framework is applied by projecting the recovered FECG signals onto a wavelet dictionary comprised of shifted Kronecker delta functions and reconstructing the distortion minimized FECG signal along with low-pass filtering of the FECG signal (see, for example, steps 412-416). The results in this example indicate a minimization of distortion effects using as little as 4% of the basis elements from the wavelet dictionary.

Figure 11:
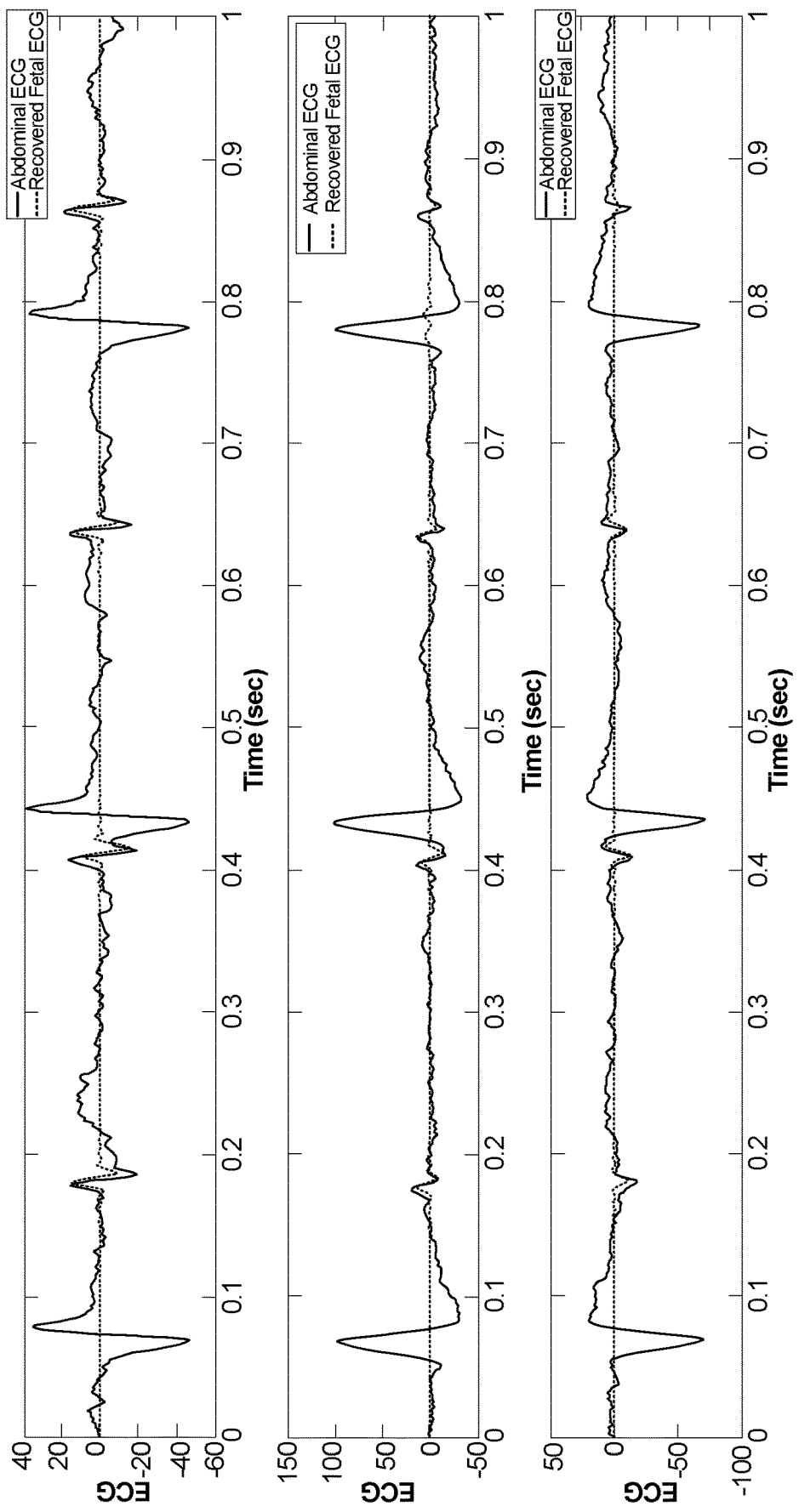
FIG. 11 illustrates the plurality of estimated FECG signals as a result of dual-dictionary framework and filtering of the plurality of FECG signals according to an embodiment of the present invention.

FIG. 11 illustrates the plurality of individual FECG signals recovered after completion of all steps described, for example, with respect to FIG. 4. Once again, the abdominal ECG signals monitored by the plurality of ECG sensors are illustrated in blue while the plurality of recovered FECG signals following application of the dual-dictionary framework and subsequent filtering are illustrated in red.

Figure 12:
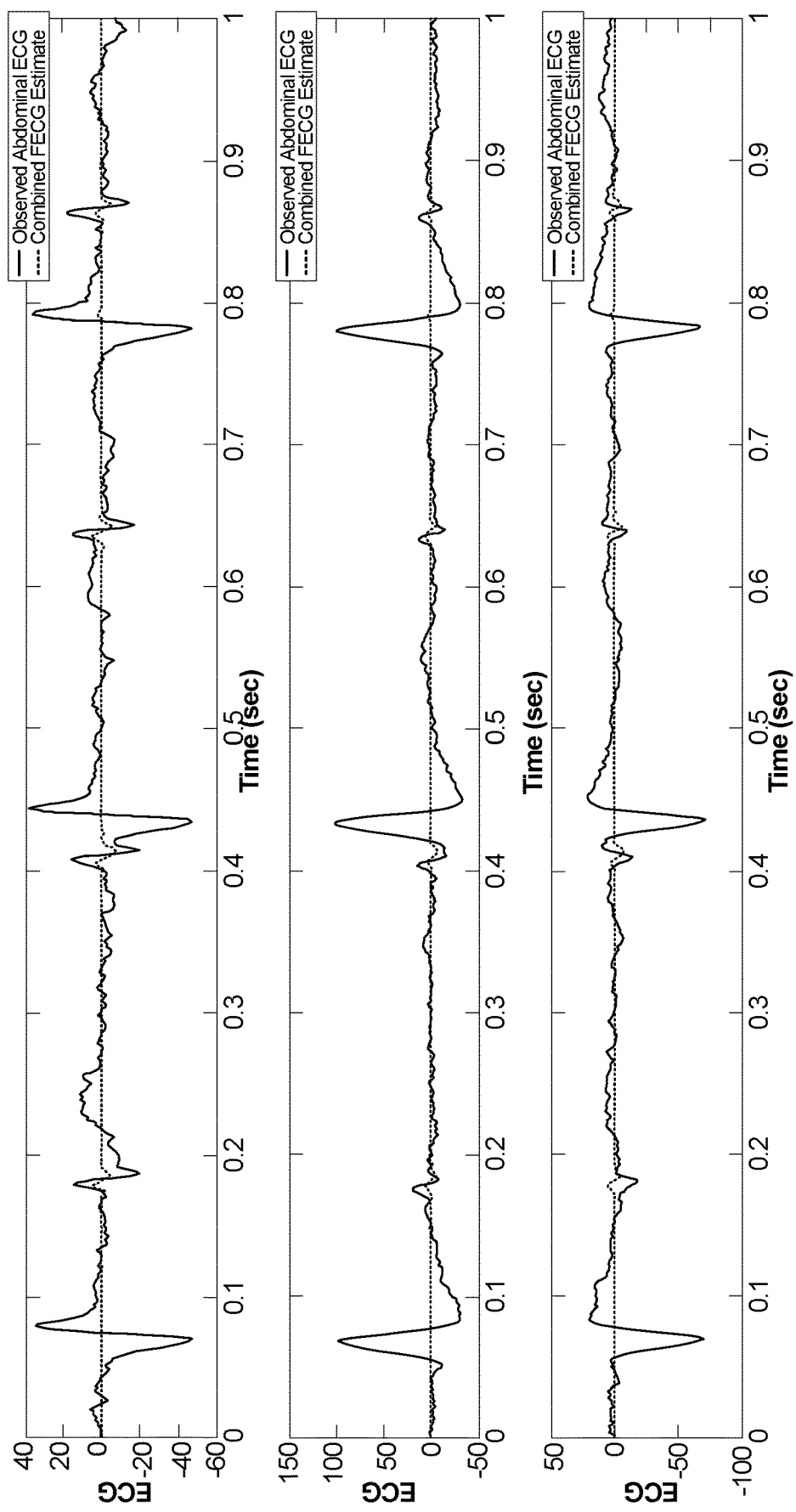
FIG. 12 illustrates the combination of the plurality of estimated FECG signals into a single estimate of the FECG source signal as compared to the plurality of ECG signals monitored by the plurality of ECG sensors located on the patient's abdomen.

FIG. 12 illustrates the combination of the plurality of FECG signals into a single FECG signal and compares the combined estimate of the FECG signal with the plurality of ECG signals monitored by the plurality of ECG sensors (abdominal). Once again, the abdominal ECG signals monitored by the plurality of ECG sensors are illustrated in blue while the combined FECG signal—which is compared to each of the plurality of abdominal ECG signals—is illustrated in red. In particular, while the embodiment shown in FIG. 11 illustrated that each of the plurality of recovered FECG signals may differ slightly, the combination of the plurality of FECG signals results in a single estimate of the recovered FECG signal.

In one embodiment, the combination of the plurality of recovered FECG signals is provided as described with respect to FIG. 5. For example, this may include calibrating the scales and alignment (e.g., normalized weights) of the plurality of recovered FECG signals such that the residuals between the observed and reconstructed abdominal signals are minimized. Common support for all sensor estimates are determined, for example, using the M-SABMP algorithm and the weights obtained from the residual calculation are used to combine the individual sensor estimates to provide the final estimate of the FECG source signal. As illustrated in the example shown in FIG. 12, the combined FECG estimate successfully removes the MECG components of the monitored ECG signals and reduces noise and distortions, providing a very clean and accurate estimate of the FECG source signal.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of estimating fetal electrocardiogram (FECG) signals and distinguishing from a mother's electrocardiogram (MECG) signals, based on a plurality of abdominal ECG signals measured by electrodes configured to be located on a mother's abdomen, the method comprising:
    defining an MECG dictionary of symbols representing the MECG signal in the sparse domain, wherein defining the MECG dictionary of symbols includes utilizing a plurality of chest ECG signals representative of the MECG signal to learn the MECG dictionary of symbols;
    projecting the plurality of abdominal ECG signals onto the MECG dictionary of symbols to estimate MECG signals within the plurality of abdominal ECG signals;
    subtracting the estimated MECG signals from the plurality of abdominal ECG signals to generate a plurality of estimated FECG signals; and
    combining the plurality of estimated FECG signals to generate a representation of the estimated FECG signal.

2. The method of claim 1, wherein projecting the plurality of abdominal ECG signals onto the MECG dictionary of symbols to estimate MECG signals within the plurality of abdominal ECG signals includes utilizing a multiple measurement vector (MMV) framework to estimate MECG components in a sparse domain.

3. The method of claim 2, wherein projecting the plurality of abdominal ECG signals onto the MECG dictionary of symbols to estimate MECG signals within the plurality of abdominal ECG signals further includes reconstructing the estimated MECG components in a time-domain using a MMV reconstruction algorithm.

4. The method of claim 1, wherein combining the plurality of estimated FECG signals includes:
    quantifying a quality of each of the plurality of estimated MECG signals and each of the plurality of estimated FECG signals; and
    linearly combining the plurality of estimated FECG signals based, in part, on the quantified quality of the plurality of estimated MECG signals and the plurality of estimated FECG signals.

5. The method of claim 4, wherein combining the plurality of estimated FECG signals further includes calculating a common support vector for each of the plurality of estimated FECG signals.

6. The method of claim 4, wherein the quantified quality of the plurality of estimated MECG signals and the plurality of estimated FECG is a normalized weight.

7. The method of claim 1, further including:
    defining a dictionary of FECG symbols representing estimated FECG signals in a sparse domain; and
    reconstructing the estimated FECG signals from the sparse domain.

8. The method of claim 7, wherein the dictionary of FECG signals is a dictionary of wavelet basis elements.

9. The method of claim 1, wherein the method is non-invasive.

10. A system for estimating fetal electrocardiogram (FECG) signal, the system comprising:
    a first plurality of electrodes connected to measure a first plurality of ECG signals;
    a second plurality of electrodes connected to measure a second plurality of ECG signals; and
    an ECG processing system configured to receive the first plurality of measured ECG signals and the second plurality of measured ECG signals, wherein the ECG processing system defines a MECG dictionary of symbols representing the mother's ECG in the sparse domain based on the first plurality of measured ECG signals, and projects the second plurality of measured ECG signals onto the MECG dictionary to estimate MECG signals within the second plurality of measured ECG signals, subtracts the estimated MECG signals from the second plurality of measured ECG signals to obtain a plurality of estimated FECG signals, wherein the plurality of estimated FECG signals are combined to generate a representation of the estimated FECG signal.

11. The system of claim 10, wherein the first plurality of electrodes and the second plurality of electrodes are included as part of a wearable system.

12. The system of claim 10, further including an external device wirelessly coupled to the ECG processing system to receive information regarding the estimated FECG signal extracted by the ECG processing system.

13. The system of claim 12, wherein the external device is a smartphone.

14. The system of claim 12, wherein the external device displays the extracted FECG source signal, communicates data/alerts to a physician/caregiver, records the extracted FECG source signal, and/or analyzes the extracted FECG source signal.

15. The system of claim 10, wherein the ECG processing system utilizes a multiple measurement vector (MMV) framework to projects the second plurality of measured ECG signals onto the MECG dictionary to estimate MECG components in a sparse domain.

16. The system of claim 15, wherein the ECG processing system reconstructs the estimated MECG components in a time-domain using a MMV reconstruction algorithm.

17. The system of claim 10, wherein the first plurality of electrodes is placed where a fetal component of the first plurality of measured ECG signals is known to be insignificant.

18. The system of claim 10, wherein the ECG processing system further processes the estimated FECG signal to minimize effects of distortion.

* * * * *